United States Patent
Naito

(10) Patent No.: US 11,992,185 B2
(45) Date of Patent: May 28, 2024

(54) INSERTION INSTRUMENT, ENDOSCOPE

(71) Applicant: OLYMPUS CORPORATION, Tokyo (JP)

(72) Inventor: Kimihiko Naito, Kawasaki (JP)

(73) Assignee: OLYMPUS CORPORATION, Tokyo (JP)

( * ) Notice: Subject to any disclaimer, the term of this patent is extended or adjusted under 35 U.S.C. 154(b) by 795 days.

(21) Appl. No.: 17/030,861

(22) Filed: Sep. 24, 2020

(65) Prior Publication Data

US 2021/0068618 A1    Mar. 11, 2021

Related U.S. Application Data

(63) Continuation of application No. PCT/JP2018/033078, filed on Sep. 6, 2018.

(30) Foreign Application Priority Data

Mar. 29, 2018 (JP) ................................ 2018-064864

(51) Int. Cl.
*A61B 1/00* (2006.01)
*A61M 25/01* (2006.01)

(52) U.S. Cl.
CPC ........ *A61B 1/0016* (2013.01); *A61B 1/00154* (2013.01); *A61M 25/0113* (2013.01)

(58) Field of Classification Search
CPC ............. A61B 1/0016; A61B 1/00154; A61M 25/0113
See application file for complete search history.

(56) References Cited

U.S. PATENT DOCUMENTS

| 6,475,222 | B1 * | 11/2002 | Berg ..................... A61M 25/10 606/108 |
| 2006/0200191 | A1 * | 9/2006 | Zadno-Azizi ...... A61M 25/1011 604/101.05 |
| 2009/0281384 | A1 | 11/2009 | Tsumaru et al. |
| 2014/0336594 | A1 | 11/2014 | Tano et al. |
| 2016/0222261 | A1 * | 8/2016 | Yokoyama ................ B32B 7/12 |
| 2017/0202434 | A1 | 7/2017 | Mitamura |

(Continued)

FOREIGN PATENT DOCUMENTS

| EP | 1 900 318 A1 | 3/2008 |
| EP | 3 320 826 A1 | 5/2018 |
| JP | 2008-068025 A | 3/2008 |

(Continued)

OTHER PUBLICATIONS

International Search Report dated Nov. 27, 2018 received in PCT/JP2018/033078.

*Primary Examiner* — Anh Tuan T Nguyen
*Assistant Examiner* — Rynae E Boler
(74) *Attorney, Agent, or Firm* — Scully, Scott, Murphy & Presser, P.C.

(57) ABSTRACT

An insertion instrument includes an insertion portion, a tubular member that rotates about a longitudinal axis by a transmitted driving force, a flange portion that holds a position of the tubular member at an outer periphery of the insertion portion, a tapered portion having an outer diameter that gradually decreases toward a proximal end side, and an adhesive layer formed to smoothly connect a proximal end portion of the tapered portion and an outer periphery of the insertion portion.

18 Claims, 5 Drawing Sheets

(56) References Cited

U.S. PATENT DOCUMENTS

2017/0279237 A1* 9/2017 Ishizaki ............ A61B 1/00148

FOREIGN PATENT DOCUMENTS

| JP | 2013-158542 A | 8/2013 | |
|---|---|---|---|
| JP | 2015-117283 A | 6/2015 | |
| WO | 2013/118649 A1 | 8/2013 | |
| WO | WO-2016194452 A1 * | 12/2016 | ......... A61B 1/00073 |
| WO | 2017/006598 A1 | 1/2017 | |

* cited by examiner

INSERTION INSTRUMENT, ENDOSCOPE

CROSS REFERENCE TO RELATED APPLICATION

This application is a continuation application of PCT/JP2018/033078 filed on Sep. 6, 2018 and claims benefit of Japanese Application No. 2018-064864 filed in Japan on Mar. 29, 2018, the entire contents of which are incorporated herein by this reference.

BACKGROUND OF THE INVENTION

1. Field of the Invention

The present invention relates to an insertion instrument and an endoscope which include a tubular member disposed at an outer periphery of an insertion portion.

2. Description of the Related Art

An insertion instrument including an insertion portion to be inserted into a subject, such as a living organism or a structure, to make an observation or perform a treatment within the subject is used in, for example, medical and industrial fields. Such an insertion instrument includes an endoscope as disclosed in, for example, International Publication No. WO 2017/006598.

The endoscope disclosed in International Publication No. WO 2017/006598 has a configuration for rotating a tubular member that is rotated at an outer periphery of an insertion portion. Further, the endoscope disclosed in International Publication No. WO 2017/006598 includes a flange portion that projects from the insertion portion so as to hold a position of the tubular member with respect to the insertion portion. The technique disclosed in International Publication No. WO 2017/006598 prevents the generation of a step in a radial direction on the insertion portion due to the formation of a tapered surface on the flange portion.

SUMMARY OF THE INVENTION

An insertion instrument according to an aspect of the present invention includes an insertion portion extending along a longitudinal axis; a tubular member formed in a tubular shape along the longitudinal axis in the insertion portion, the tubular member being configured to rotate about the longitudinal axis by a transmitted driving force; a flange portion that holds a position of the tubular member in a direction of the longitudinal axis at an outer periphery of the insertion portion; a tapered portion provided on a proximal end side of the flange portion in the direction of the longitudinal axis, an outer diameter of the tapered portion gradually decreasing toward the proximal end side; and an adhesive layer formed to smoothly connect a proximal end portion of the tapered portion and an outer periphery of the insertion portion.

An insertion instrument according to another aspect of the present invention includes an insertion portion extending along a longitudinal axis; a flange portion that holds a position of a tubular member in a direction of the longitudinal axis at an outer periphery of the insertion portion when the tubular member is mounted on the insertion portion, the tubular member being formed in a tubular shape along the longitudinal axis in the insertion portion and being configured to rotate about the longitudinal axis by a transmitted driving force; a tapered portion provided on a proximal end side of the flange portion in the direction of the longitudinal axis, an outer diameter of the tapered portion gradually decreasing toward the proximal end side; and an adhesive layer formed to smoothly connect a proximal end portion of the tapered portion and an outer periphery of the insertion portion.

An endoscope according to an aspect of the present invention includes an insertion portion extending along a longitudinal axis; a tubular member formed in a tubular shape along the longitudinal axis in the insertion portion, the tubular member being configured to rotate about the longitudinal axis by a transmitted driving force; a flange portion that holds a position of the tubular member in a direction of the longitudinal axis at an outer periphery of the insertion portion; a tapered portion provided on a proximal end side of the flange portion in the direction of the longitudinal axis, an outer diameter of the tapered portion gradually decreasing toward the proximal end side; and an adhesive layer formed to smoothly connect a proximal end portion of the tapered portion and an outer periphery of the insertion portion.

An endoscope according to another aspect of the present invention includes an insertion portion extending along a longitudinal axis; a flange portion that holds a position of a tubular member in a direction of the longitudinal axis at an outer periphery of the insertion portion when the tubular member is mounted on the insertion portion, the tubular member being formed in a tubular shape along the longitudinal axis in the insertion portion and being configured to rotate about the longitudinal axis by a transmitted driving force; a tapered portion provided on a proximal end side of the flange portion in the direction of the longitudinal axis, an outer diameter of the tapered portion gradually decreasing toward the proximal end side; and an adhesive layer formed to smoothly connect a proximal end portion of the tapered portion and an outer periphery of the insertion portion.

DETAILED DESCRIPTION OF THE PREFERRED EMBODIMENTS

Figure 1:
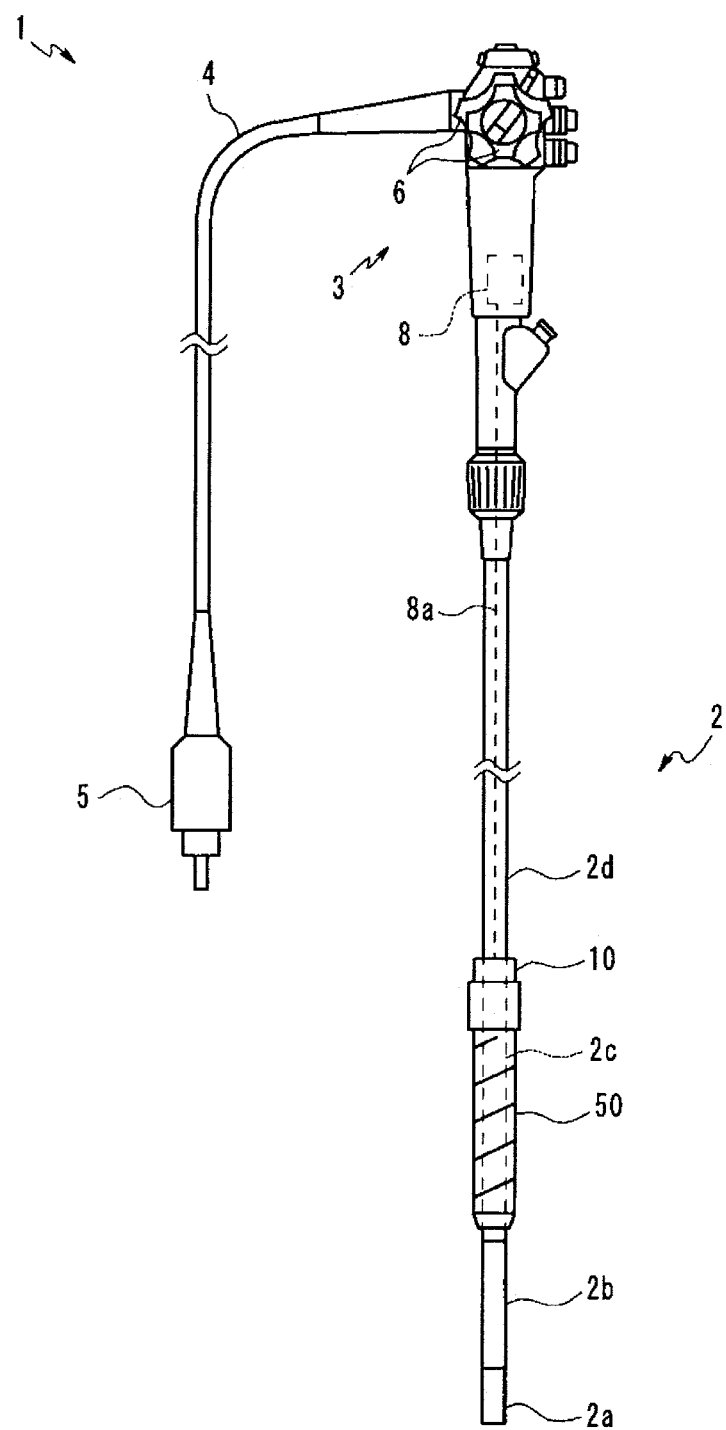
FIG. 1 is a view illustrating a configuration of an endoscope serving as an insertion instrument.

Preferred modes of the present invention will be described below with reference to the drawings. Note that in the drawings used in the following description, the constituent elements are illustrated at different scales so that each constituent element is illustrated with a recognizable size in the drawings. The present invention is not limited only to the number of constituent elements illustrated in the drawings, the shapes of the constituent elements, the ratios between the sizes of the constituent elements, and relative positional relationships among the constituent elements.

An endoscope 1 serving as an insertion instrument illustrated in FIG. 1 includes an elongated insertion portion (elongated body) 2 that can be introduced into a subject, such as a human body. The insertion portion 2 has a configuration for observing the inside of the subject. Note that the subject into which the insertion portion 2 of the endoscope 1 is introduced is not limited to a human body, but instead may be a living organism other than a human body, or an artifact such as a machine or a building. Further, the insertion instrument is not limited to an endoscope, but instead may be a treatment instrument for, for example, performing an excision or suction within the subject.

The present embodiment illustrates an example where the endoscope 1 is an endoscope for medical use. The endoscope 1 includes the insertion portion 2 extending along a longitudinal axis, an operation portion 3 located at a proximal end, which is one end of the insertion portion 2, a universal cord 4 extending from the operation portion 3, and a tubular member (tubular body) 50 disposed at an outer periphery of the insertion portion 2.

The insertion portion 2 has a configuration in which a distal end portion 2a, a bending portion 2b, a first flexible tube portion 2c, a power transmission portion 10, and a second flexible tube portion 2d are connected in this order from a distal end to a proximal end.

The distal end portion 2a is provided with, for example, a configuration for observing the inside of the subject. Specifically, the distal end portion 2a is provided with an image pickup apparatus that includes an objective lens and an image pickup device so as to optically observe the inside of the subject. The distal end portion 2a is also provided with an illumination light emission portion that emits light for illuminating an object for the image pickup apparatus. Note that the distal end portion 2a may be provided with an ultrasonic transducer for acoustically observing the inside of the subject using ultrasonic waves. The bending portion 2b is bent along with a rotation of an operation knob 6 that is provided on the operation portion 3. The configuration of each of the distal end portion 2a and the bending portion 2b is similar to that of a known endoscope, and thus the detailed description thereof is omitted.

The first flexible tube portion 2c and the second flexible tube portion 2d have flexibility and thus are bent depending on an external force to be applied. On the other hand, the power transmission portion 10 that connects the first flexible tube portion 2c and the second flexible tube portion 2d has rigidity and thus is not bent.

The power transmission portion 10 is coupled with the tubular member 50 disposed at the outer periphery of the first flexible tube portion 2c. The power transmission portion 10 transmits power generated by an actuator 8, such as an electric motor, which is included in the endoscope 1, to the tubular member 50. The actuator 8 is capable of switching whether to generate power depending on an operation of a switch that is not illustrated.

A drive shaft 8a is inserted into each of the operation portion 3 and the second flexible tube portion 2c. The drive shaft 8a has flexibility and is rotated about the longitudinal axis by the power generated by the actuator 8. The drive shaft 8a transmits the power generated by the actuator 8 to the power transmission portion 10.

The tubular member 50 is rotated about the insertion portion 2 with respect to the first flexible tube portion 2c by the power generated by the actuator 8. The configuration of the power transmission portion 10 will be described below.

A proximal end portion of the universal cord 4 is provided with an endoscope connector 5 configured to be connectable to an external device that is not illustrated. The external device to which the endoscope connector 5 is connected includes a camera control unit that controls the image pickup apparatus provided at the distal end portion 2a.

Figure 2:
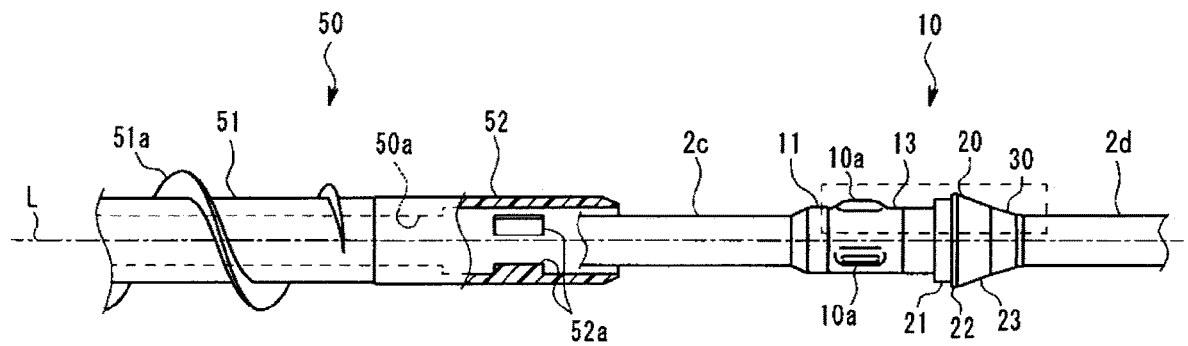
FIG. 2 is a view illustrating a tubular member and a power transmission portion in a state where the tubular member is dismounted.
Figure 3:
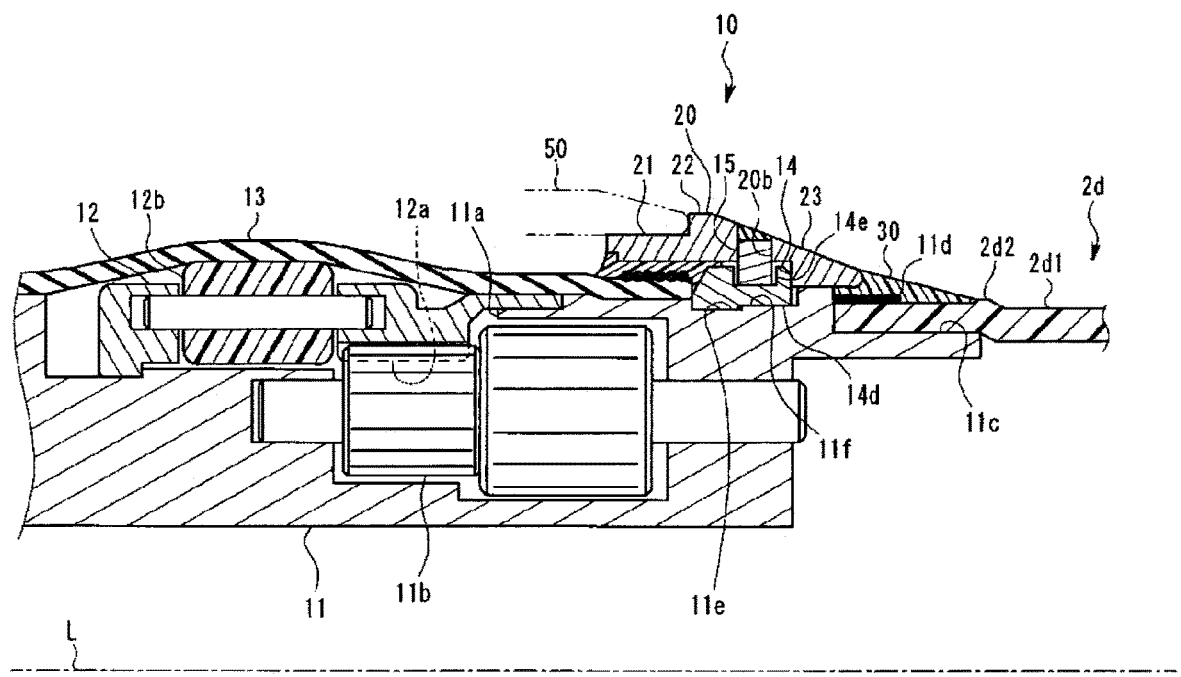
FIG. 3 is a sectional view of the power transmission portion.

FIG. 2 is an external view of the tubular member 50 and the power transmission portion 10 in a state where the tubular member 50 is dismounted. A dashed-dotted line illustrated in FIG. 2 represents a longitudinal axis L of the insertion portion 2. FIG. 3 is a partial sectional view of the power transmission portion 10. FIG. 3 illustrates a section of a portion surrounded by a dashed square in FIG. 2 in a plane parallel to the longitudinal axis L. In FIGS. 2 and 3, the left side along the longitudinal axis L corresponds to a distal end side, and the right side along the longitudinal axis L corresponds to a proximal end side.

As illustrated in FIG. 3, the power transmission portion 10 includes a body frame 11, a rotary ring 12, a coating member 13, a fixed ring 20, and an adhesive layer 30.

The body frame 11 is a tubular member that connects a proximal end of the first flexible tube portion 2c and a distal end of the second flexible tube portion 2d. In other words, the body frame 11 is fixed to the insertion portion 2. The rotary ring 12, the coating member 13, the fixed ring 20, and the adhesive layer 30 are disposed in the vicinity of the body frame 11.

The body frame 11 is a rigid member made of a material having a predetermined rigidity, such as metal, resin, or ceramic. Note that although FIG. 3 illustrates the body frame 11 as a single member, the body frame 11 may be divided into a plurality of members.

The body frame 11 is provided with an opening portion 11a that is opened toward the outside of the insertion portion 2 in a radial direction. Note that the outside of the insertion portion 2 in the radial direction indicates a direction from the inside of the insertion portion 2 to the outside of the insertion portion 2 along an axis perpendicular to the longitudinal axis L.

A drive gear 11b is disposed in the opening portion 11a. The drive gear 11b is an external gear. The drive gear 11b is supported on the body frame 11 such that the drive gear is rotatable about an axis parallel to the longitudinal axis L. A part of a tooth surface of the drive gear 11b is exposed to the outside of the body frame 11 through the opening portion 11a.

A rotation axis of the drive gear 11b is connected to a distal end of the drive shaft 8a inserted into the second flexible tube portion 2d. A proximal end of the drive shaft 8a is connected to the actuator 8. The drive shaft 8a transmits the power generated by the actuator 8 to the drive gear 11b. In other words, when the actuator 8 generates power, the drive gear 11b is rotated.

A proximal end of the body frame 11 is provided with a cylindrical coupling portion 11c. The coupling portion 11c is a portion to which an outer coat 2d1 of the second flexible tube portion 2d is fitted. The outer coat 2d1 is a tubular member that is mainly made of resin and has flexibility. The outer coat 2d1 forms the outer surface of the second flexible tube portion 2d.

Note that although FIG. 3 illustrates the outer coat 2d1 as a single member, the outer coat 2d1 may be formed by superimposing a plurality of members in a thickness direction. In addition, a surface treatment, such as coating containing, for example, fluorine, may be performed on the outer peripheral surface of the outer coat 2d1.

The coupling portion 11c is press-fitted from an opening formed at a distal end of the outer coat 2d1 such that the opening is pushed out. An adhesive for enhancing the coupling strength and watertightness between the coupling portion 11c and the outer coat 2d1 may be disposed between an outer peripheral surface of the coupling portion 11c and an inner peripheral surface of the outer coat 2d1.

The present embodiment illustrates an example where a bobbin portion 11d is provided on the outer peripheral surface of the portion where the coupling portion 11c of the outer coat 2d1 is press-fitted. The bobbin portion 11d is a portion around which a thread is wound a plurality of times such that the portion where the coupling portion 11c of the outer coat 2d1 is press-fitted is tightened. The bobbin portion 11d enhances the coupling strength and watertightness between the coupling portion 11c and the outer coat 2d1.

The rotary ring 12 is an annular member that is disposed at the outer periphery of the body frame 11 and is rotated about the longitudinal axis L with respect to the body frame 11.

A driven gear 12a that meshes with the drive gear 11b is provided at the inner periphery of the rotary ring 12. The driven gear 12a is an internal gear. Accordingly, the rotary ring 12 is rotated about the longitudinal axis L depending on the rotation of the drive gear 11b.

The rotary ring 12 is provided with a plurality of rollers 12b. Each roller 12b is supported on the rotary ring 12 such that the roller can be rotated about an axis parallel to the longitudinal axis L. The rotation axes of the plurality of rollers 12b are disposed at predetermined intervals on a circle centered on the longitudinal axis L in a plane perpendicular to the longitudinal axis L. As illustrated in FIG. 3, the rollers 12b project toward the outside in the radial direction from the outer periphery of the body frame 11.

The coating member 13 is a tubular film for coating the outer periphery of each of the body frame 11 and the rotary ring 12. The coating member 13 is made of an elastic deformable material such as rubber. The coating member 13 forms a part of the outer surface of the power transmission portion 10. The coating member 13 prevents liquid, foreign matter, or the like from entering the insertion portion 2 through the opening portion 11a of the body frame 11. The coating member 13 is fixed to the body frame 11. Accordingly, the rotary ring 12 is rotated in contact with the inner peripheral surface of the coating member 13 on the inside of the coating member 13.

Since the coating member 13 is an elastic deformable film, as illustrated in FIG. 2, engagement projections 10a each projecting toward the outside in the radial direction on the outer surface of the power transmission portion 10 are formed at portions where the rollers 12b are in contact with the inside of the coating member 13. The position of each engagement projection 10a is moved about the longitudinal axis L along with the rotary ring 12.

Figure 5:
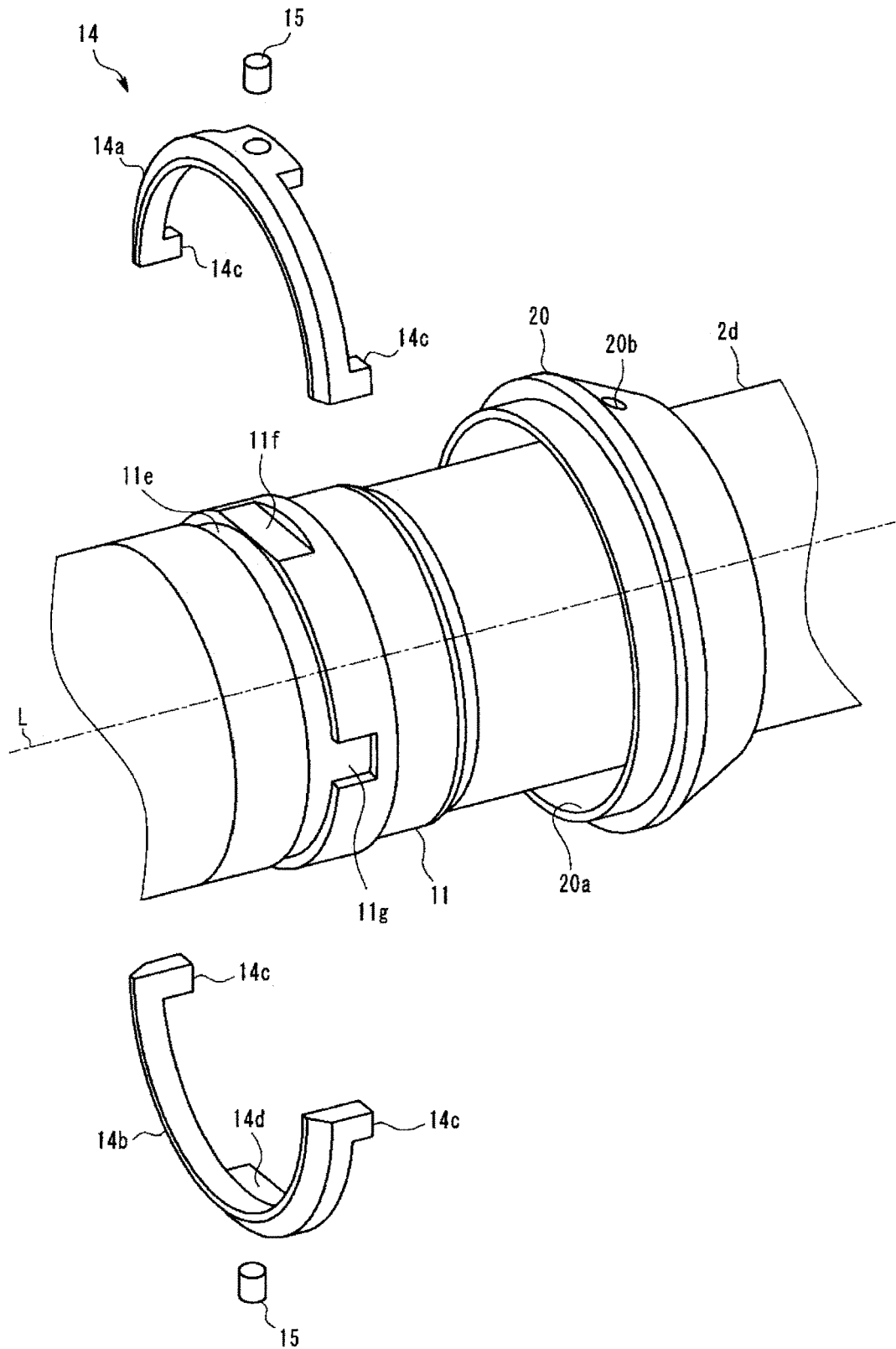
FIG. 5 is an exploded view of a configuration for fixing a fixed ring to a body frame.

The fixed ring 20 is an annular member fixed to the outer periphery of the body frame 11. The fixed ring 20 is disposed on the proximal end side of each engagement projection 10a. As illustrated in FIG. 5, the fixed ring 20 includes a through-hole 20a through which the proximal-end-side portion of the body frame 11 can be inserted. The fixed ring 20 is a rigid member made of a material having a predetermined rigidity, such as metal, resin, or ceramic.

The fixed ring 20 is formed such that a sliding portion 21, a flange portion 22, and a tapered portion (tapered surface) 23 are contiguous in this order from the distal end side to the proximal end side. The present embodiment illustrates an example where the fixed ring 20 is a single member.

The sliding portion 21 is a cylindrical portion centered on the longitudinal axis L. The outer diameter of the sliding portion 21 is substantially equal to or greater than that of a circle circumscribed on the plurality of engagement projections 10a. A connector portion 52 to be described below of the tubular member 50 is in slidable contact with the outer periphery of the sliding portion 21.

The flange portion 22 is a portion that projects toward the outside of the sliding portion 21. Specifically, the flange portion 22 has a cylindrical outer peripheral shape centered on the longitudinal axis L. In other words, the outer diameter of the flange portion 22 is greater than that of the sliding portion 21. Further, the outer diameter of the flange portion 22 is greater than the outer diameter of the second flexible tube portion 2d. The flange portion 22 is brought into contact with the proximal end of the tubular member 50, thereby holding the position of the tubular member 50 in the direction along the longitudinal axis L with respect to the insertion portion 2.

The tapered portion 23 is a conical portion centered on the longitudinal axis L. The outer diameter of the tapered portion 23 gradually decreases toward the proximal end side along the longitudinal axis L. The outer diameter of the distal end of the tapered portion 23 is equal to that of the flange portion 22. On the other hand, the outer diameter of the proximal end of the tapered portion 23 is smaller than the outer diameter of the distal end thereof, but is greater than the outer diameter of the second flexible tube portion 2d.

The flange portion 22 is a portion having a largest outer diameter in the insertion portion 2 in a state where the tubular member 50 is dismounted. The tapered portion 23 prevents a step from being generated due to a difference between the outer diameter of the flange portion 22 and the outer diameter of the second flexible tube portion 2d located on the proximal end side of the flange portion 22. The term "step" used herein refers to a rapid change in the outer diameter of the insertion portion 2 in the direction along the longitudinal axis L.

In the present embodiment, a part of the proximal end side of the tapered portion 23 overlaps the outside of the coupling portion 11c. Specifically, the distal end of the outer coat 2d1 that covers the outer periphery of the coupling portion 11c is located at a position closer to the distal end side than the proximal end portion of the tapered portion 23. Therefore, in the present embodiment, the proximal end portion of the tapered portion 23 is located on the outside in the radial direction with respect to the outer peripheral surface of the outer coat 2d1, and a step still exists between the proximal end portion of the tapered portion 23 and the outer peripheral surface of the outer coat 2d1.

The adhesive layer 30 is formed to smoothly connect the proximal end portion of the tapered portion 23 and the outer peripheral surface of the outer coat 2d1. The adhesive layer 30 has a conical outer shape that fills the step between the proximal end portion of the tapered portion 23 and the outer peripheral surface of the outer coat 2d1, and has an outer diameter that gradually decreases toward the proximal end side.

Further, in the present embodiment, the adhesive layer 30 is formed to cover not only the outer periphery of the outer coat 2d1, but also the bobbin portion 11d. The adhesion strength of the adhesive layer 30 with respect to the bobbin portion 11d is lower than the adhesion strength of the adhesive layer 30 with respect to the outer periphery of the outer coat 2d1. This facilitates a work for removing the adhesive layer 30 in the case of disassembling the power transmission portion 10, for example, during maintenance of the endoscope 1.

Figure 4:
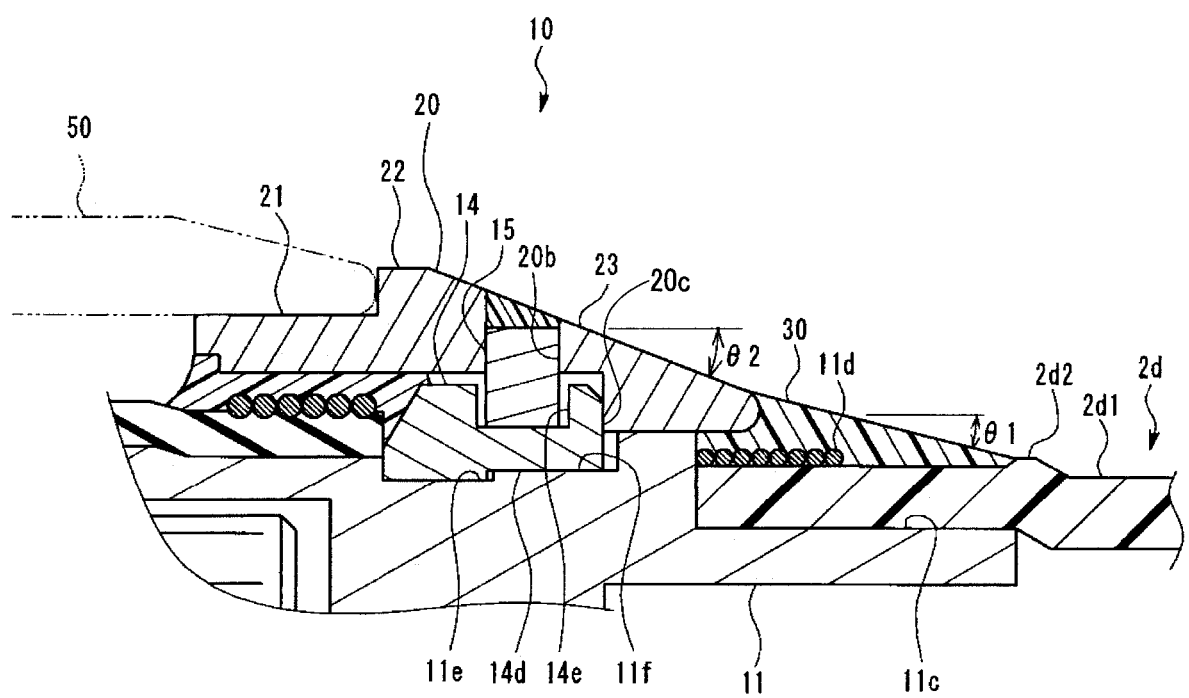
FIG. 4 is an enlarged view of a part of FIG. 3.

FIG. 4 is an enlarged view of a portion corresponding to the tapered portion 23 and the adhesive layer 30 illustrated in FIG. 3. In the present embodiment, an angle θ1 with respect to the longitudinal axis L of the outer surface of the adhesive layer 30 is smaller than an angle θ2 with respect to the longitudinal axis L of the conical surface of the tapered portion 23 at a section in a plane including the longitudinal axis L. In other words, a variation in the outer diameter at a predetermined distance in the direction along the longitudinal axis L in the adhesive layer 30 is smaller than a variation in the outer diameter at a predetermined distance in the direction along the longitudinal axis L in the tapered portion 23. Like in the present embodiment, the inclination of the adhesive layer 30 is set to be less than the inclination of the tapered portion 23, thereby preventing the power transmission portion 10 from being easily hooked on a narrowed portion or a convex portion when the insertion portion 2 moved in the proximal end direction within the subject.

Further, in the present embodiment, during assembly of the endoscope 1, a convex portion 2d2, which is an index for coating the adhesive layer 30 so as to have a conical shape as described above, is formed at the outer periphery of the outer coat 2d1. The convex portion 2d2 is provided at a position at a predetermined distance along the longitudinal axis L from the distal end of the outer coat 2d1. The convex portion 2d2 is formed on the entire circumferential area at the outer periphery of the outer coat 2d1.

The convex portion 2d2 indicates a position at the proximal end of the adhesive layer 30. If the adhesive layer is coated in a range from the proximal end portion of the tapered portion 23 to the position of the convex portion 2d2 during assembly of the endoscope 1, the inclination of the adhesive layer 30 can be reliably set to be less than the inclination of the tapered portion 23. Further, the adhesive layer 30 is formed based on the convex portion 2d2, thereby making it possible to suppress variations in the shape of the adhesive layer 30.

Note that the method of forming the convex portion 2d2 is not particularly limited. For example, the convex portion 2d2 can be formed by cutting the coating formed at the outer periphery of the outer coat 2d1.

Further, in the present embodiment, the proximal end of the adhesive layer 30 is disposed at a position closer to the distal end side than the proximal end of the coupling portion 11c that is press-fitted in the outer coat 2d1. In other words, the rigid coupling portion 11c is press-fitted in the portion covered by the adhesive layer 30 of the outer coat 2d1. In other words, in the present embodiment, the adhesive layer 30 is disposed to cover only the area in which the outer coat 2d1 is not bent. According to the present embodiment as described above, the adhesion surface between the adhesive layer 30 and the outer coat 2d1 is not deformed when the endoscope 1 is used, thereby preventing a gap from being formed between the adhesive layer 30 and the outer coat 2d1.

Further, in the present embodiment, the proximal end of the tapered portion 23 has a rounded R-shape. The proximal end of the tapered portion 23 is formed in the R-shape, thereby enabling the formation of the outer surface of the tapered portion 23 and the outer surface of the adhesive layer 30 disposed around the tapered portion 23 in a smoothly continuous manner.

Next, the configuration of the tubular member 50 will be described. As illustrated in FIG. 2, the tubular member 50 has a cylindrical shape provided with a through-hole 50a into which the first flexible tube portion 2c is inserted. The tubular member 50 has a configuration in which a deformable portion 51, which is provided on the distal end side and has flexibility, and the rigid connector portion 52 provided on the proximal end side are contiguous in the direction along the longitudinal axis L.

The deformable portion 51 has flexibility and is thus bent with the first flexible tube portion 2c inserted into the through-hole 50a. A fin 51a is provided at the outer periphery of the deformable portion 51. The fin 51a has a spiral shape with the longitudinal axis L as a central axis. In other words, the fin 51a has a shape corresponding to a ridge portion of an external thread.

The connector portion 52 is a cylindrical portion that is in slide contact with the outer periphery of the sliding portion 21 of the power transmission portion 10. The inner diameter of the connector portion 52 is greater than the outer diameter of the sliding portion 21 and is smaller than the outer diameter of the flange portion 22. Accordingly, the connector portion 52 is brought into contact with the flange portion 22, thereby positioning the tubular member 50 in the direction along the longitudinal axis L with respect to the insertion portion 2. Further, the connector portion 52 can be rotated about the longitudinal axis L around the sliding portion 21.

A plurality of engagement claws 52a projecting toward the inside in the radial direction is formed on the inner peripheral surface of the connector portion 52. Each engagement claw 52a is disposed at a position where the engagement claw 52a engages with the corresponding engagement projection 10a in a state where the connector portion 52 is brought into contact with the flange portion 22.

As described above, each engagement projection 10a is moved about the longitudinal axis L on the outer surface of the power transmission portion 10 by the power generated by the actuator 8. The power generated by the actuator 8 is transmitted to the tubular member 50 through the engagement between the engagement projection 10a and the engagement claw 52a. Accordingly, in the endoscope 1 according to the present embodiment, the tubular member 50 can be rotated about the longitudinal axis L by the power generated by the actuator 8.

The insertion portion 2 in a state where the tubular member 50 is disposed at the outer periphery thereof is inserted into the subject and the tubular member 50 is rotated about the longitudinal axis L by the actuator 8, so that the fin 51a having a spiral shape is rotated about the longitudinal axis L within the subject. When the fin 51a is rotated in a state of being in contact with an inner wall of the subject, the tubular member 50 applies a driving force in the distal end direction or in the proximal end direction to the insertion portion 2. The application of this driving force enhances the mobility of the insertion portion 2 in the longitudinal axis direction within the subject.

As described above, the endoscope 1 serving as the insertion instrument according to the present embodiment includes the insertion portion 2 extending along the longitudinal axis L, the tubular member 50 that is formed in a tubular shape along the longitudinal axis L in the insertion portion 2 and rotates about the longitudinal axis L by a transmitted driving force, the flange portion 22 that holds the position of the tubular member 50 in the direction of the longitudinal axis L at the outer periphery of the insertion portion 2, the tapered portion 23 that is provided on the proximal end side of the flange portion 22 in the direction of the longitudinal axis L and has an outer diameter that gradually decreases toward the proximal end side, and the adhesive layer 30 that is formed to smoothly connect the proximal end portion of the tapered portion 23 and the outer periphery of the insertion portion 2.

In the endoscope 1 according to the present embodiment having a configuration as described above, the outer peripheral surface of the flange portion 22 projecting toward the outside in the radial direction from the insertion portion 2 and the outer peripheral surface of the insertion portion 2 (second flexible tube portion 2d) can be connected with continuous surfaces that are smoothly formed by the tapered portion 23 and the adhesive layer 30, each of which has a conical shape. In particular, an end of the adhesive layer 30 can be formed with a small thickness along the outer surface of the insertion portion 2, and thus even a small step formed in the radial direction in the insertion portion 2 can be eliminated. Consequently, the endoscope 1 according to the present embodiment enables a smooth movement of the insertion portion 2 within the subject.

Next, a configuration for fixing the fixed ring 20 to the body frame 11 in the power transmission portion 10 will be described. FIG. 5 is an exploded view of the configuration for fixing the fixed ring 20 to the body frame 11. In FIG. 5, the left side along the longitudinal axis L corresponds to the distal end side, and the right side along the longitudinal axis L corresponds to the proximal end side.

As illustrated in FIGS. 4 and 5, a stopper 14 is interposed between the body frame 11 and the fixed ring 20. The stopper 14 is a member that is separable from the body frame 11 and the fixed ring 20. The fixed ring 20 is fixed to the body frame 11 through the stopper 14.

Specifically, the stopper 14 is an annular member that is fitted into a groove 11e formed in the circumferential direction on the outer peripheral surface of the body frame 11. The stopper 14 is fitted into the groove 11e, thereby positioning the stopper 14 in the direction along the longitudinal axis L with respect to the body frame 11.

A flat portion 14d is formed on a part of the inner peripheral surface of the stopper 14. As illustrated in FIG. 4, a flat portion 11f to be brought into contact with the flat portion 14d is formed in the groove 11e. The flat portion 14d and the flat portion 11f are brought into contact with each other, thereby positioning the stopper 14 in the rotational direction about the longitudinal axis L with respect to the body frame 11.

The stopper 14 is a rigid member made of a material having a predetermined rigidity, such as metal, resin, or ceramic. The body frame 11 includes projecting portions that are provided on the distal end side and the proximal end side of the groove 11e and project toward the outside in the radial direction from the outer diameter of a bottom portion of the groove 11e.

The stopper 14 is divided into two members, i.e., a first member 14a and a second member 14b, so that the rigid stopper 14 is fitted into the groove 11e. Each of the first member 14a and the second member 14b has a shape obtained by equally dividing the annular stopper 14. Specifically, each of the first member 14a and the second member 14b is an arc of 180 degrees.

Locking claws 14c are formed at both ends of each of the first member 14a and the second member 14b, which have an arc shape. The locking claws 14c project in the direction along the longitudinal axis L from both ends of each of the first member 14a and the second member 14b.

Figure 6:
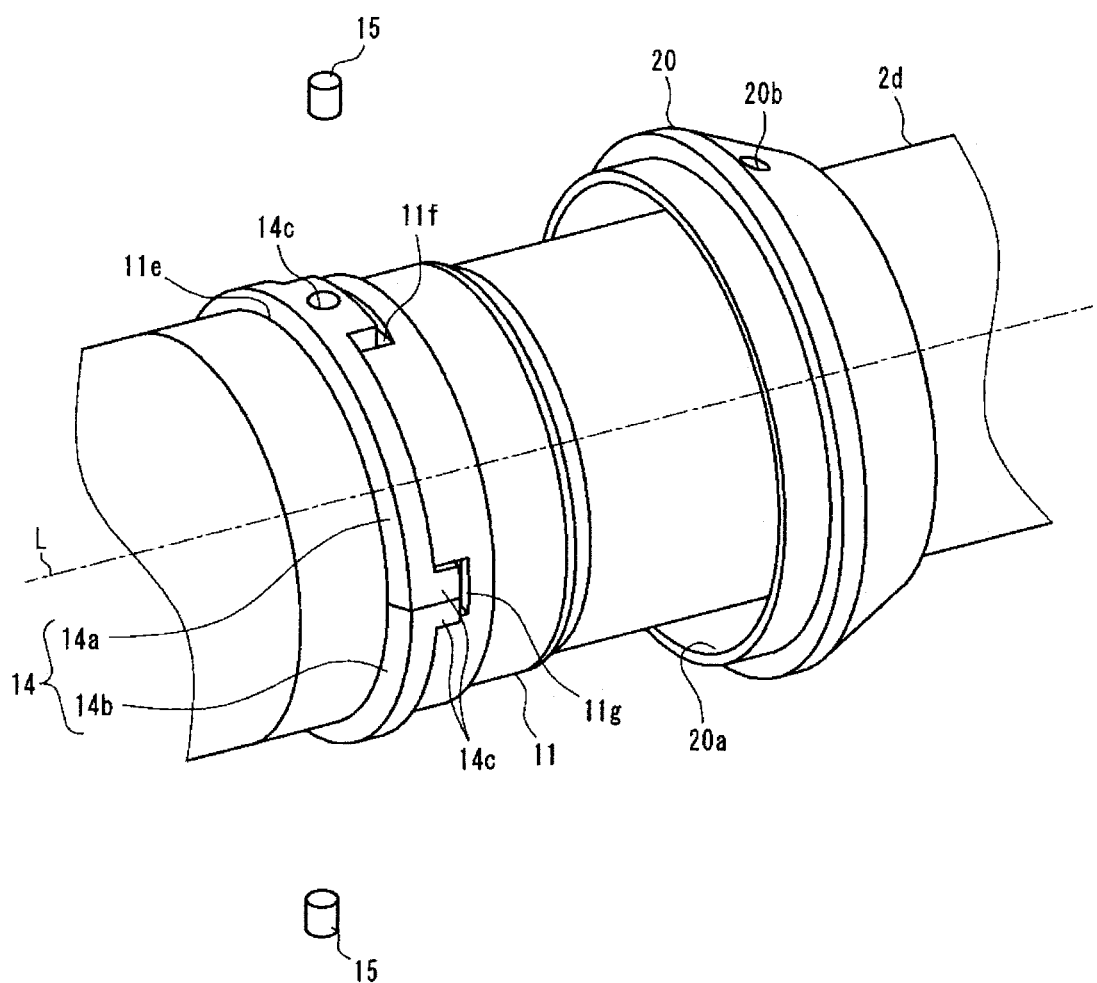
FIG. 6 is a view illustrating a state where a stopper is fitted into a groove.

Engagement concave portions 11g that engage with the locking claws 14c, respectively, are formed on a side surface portion of the groove 11e. As illustrated in FIG. 6, when the first member 14a and the second member 14b are fitted into the groove 11e, the locking claws 14c engage with the engagement concave portions 11g, respectively. The engagement between the locking claws 14c and the engagement concave portions 11g prevents the first member 14a and the second member 14b from being disengaged from the inside of the groove 11e. With this configuration, the stopper 14 divided into two members is held on the body frame 11, which facilitates a work during assembly of the endoscope 1.

Further, the stopper 14 is provided with holes 14e into which a pin 15 is fitted from the outside in the radial direction. The holes 14e are formed in both the first member 14a and the second member 14b. The fixed ring 20 is provided with a pin insertion hole 20b into which the pin 15 is inserted.

The stopper 14 has an outer diameter that enables insertion from the distal end side in the through-hole 20a of the fixed ring 20. Further, a contact surface 20c with which the proximal end of the stopper 14 is brought into contact is formed in the through-hole 20a of the fixed ring 20.

The proximal end of the stopper 14 is brought into contact with the contact surface 20c of the fixed ring 20 and the pin 15 is inserted into the pin insertion hole 20b and the hole 14e, so that the fixed ring 20 is fixed in a state where the fixed ring is positioned with respect to the stopper 14. As described above, the stopper 14 is fixed in a state where the stopper 14 is positioned with respect to the body frame 11 in the groove 11e.

With the configuration described above, the fixed ring 20 is fixed in a state where the fixed ring 20 is positioned with respect to the body frame 11. In the configuration described above, the fixed ring 20 can be fixed by being fitted to the outer periphery of the body frame 11 from the proximal end side of the body frame 11.

The present invention is not limited to the above-described embodiments and can be appropriately changed without departing from the gist or idea of the invention that can be understood from the claims and the entire specification. Insertion instruments and endoscopes with such changes are also included in the technical scope of the present invention.

What is claimed is:

1. An insertion instrument comprising:
   an insertion portion extending along a longitudinal axis; and
   a tubular body configured to be detachably attached to the insertion portion, the tubular body being configured to rotate about the longitudinal axis;
   wherein the insertion portion comprising:
      a flange configured to maintain a longitudinal position of the tubular body relative to the insertion portion;
      a tapered surface provided proximally relative to the flange, an outer diameter of the tapered surface gradually decreasing in a proximal direction, a proximal end of the tapered surface being radially separated from an outer periphery of the insertion portion to form a step; and
      an adhesive layer formed to continuously connect the proximal end of the tapered surface and the outer periphery of a portion of the insertion portion adjacent to the tapered surface, the adhesive layer being inclined relative to the longitudinal axis, the adhesive layer filling the step.

2. The insertion instrument according to claim 1, wherein the adhesive layer covers a bobbin portion provided at the outer periphery of the insertion portion.

3. The insertion instrument according to claim 1, wherein an outer surface of the adhesive layer includes a conical surface, and
   an inclination of the conical surface relative to the longitudinal axis is less than an inclination of the tapered surface relative to the longitudinal axis.

4. An insertion portion for use with an endoscope and for use with a tubular body configured to be rotatably disposed on the insertion portion, the insertion portion comprising:
- an elongated body extending along a longitudinal axis;
- a flange configured to maintain a longitudinal position of the tubular body relative to the elongated body;
- a tapered surface provided proximally relative to the flange, an outer diameter of the tapered surface gradually decreasing in a proximal direction, a proximal end of the tapered surface being radially separated from an outer periphery of the insertion portion to form a step; and
- an adhesive layer formed to continuously connect the proximal end of the tapered surface and the outer periphery of a portion of the elongated body adjacent to the tapered surface, the adhesive layer being inclined relative to the longitudinal axis, the adhesive layer filling the step.

5. An endoscope comprising the insertion instrument according to claim 1.

6. An endoscope comprising the insertion portion according to claim 4.

7. The insertion instrument according to claim 1, wherein a proximal end portion of the adhesive layer is continuously connected to the outer periphery of the insertion portion.

8. The insertion instrument according to claim 4, wherein a proximal end portion of the adhesive layer is continuously connected to the outer periphery of the elongated body.

9. The insertion instrument according to claim 1, further comprising a convex portion formed circumferentially on the outer periphery of the insertion portion.

10. The insertion instrument according to claim 9, wherein the convex portion is formed proximally relative to a bobbin portion provided at the outer periphery of the insertion portion.

11. The insertion instrument according to claim 9, wherein an outer diameter of the convex portion is larger than other portions of the insertion portion.

12. The insertion instrument according to claim 9, wherein the adhesive layer is disposed between a proximal portion of the tapered surface and a distal portion of the convex portion.

13. The insertion instrument according to claim 9, wherein a proximal end portion of the adhesive layer is continuously connected to a distal end portion of the convex portion.

14. An insertion instrument comprising:
- an insertion portion extending along a longitudinal axis; and
- a tubular body configured to be detachably attached to the insertion portion, the tubular body being configured to rotate about the longitudinal axis;

wherein the insertion portion comprising:
- a flange configured to maintain a longitudinal position of the tubular body relative to the insertion portion;
- a tapered surface provided proximally relative to the flange, an outer diameter of the tapered surface gradually decreasing in a proximal direction; and
- an adhesive layer formed to continuously connect a proximal end of the tapered surface and an outer periphery of a portion of the insertion portion, the adhesive layer being inclined relative to the longitudinal axis, wherein a distal end of the adhesive layer is provided distally relative to the proximal end of the tapered surface.

15. The insertion instrument according to claim 2, wherein a distal end of the bobbin portion is provided distally relative to the proximal end of the tapered surface.

16. The insertion instrument according to claim 2, wherein a proximal end of the bobbin portion is provided proximally relative to the proximal end of the tapered surface.

17. The insertion instrument according to claim 1, wherein the flange and the tapered surface have an annular shape.

18. The insertion instrument according to claim 1, wherein
- the adhesive layer covers a bobbin portion provided at the outer periphery of the insertion portion; and
- the bobbin portion is disposed in the step.

* * * * *